(12) United States Patent
Mederski et al.

(10) Patent No.: US 7,504,500 B2
(45) Date of Patent: Mar. 17, 2009

(54) METHOD FOR THE PRODUCTION OF PYRROLIDINE-1,2-DICARBOXYLIC ACID-1-(PHENYL(-AMIDE))-2(PHENYL(-AMIDE)) DERIVATIVES AND 1-(PHENYLCARBAMOYL)-PYRROLIDINE-2-CARBOXYLIC ACID DERIVATIVES AS INTERMEDIATE PRODUCTS

(75) Inventors: Werner Mederski, Zwingenberg (DE); Christos Tsaklakidis, Weinheim (DE); Dieter Dorsch, Ober-Ramstadt (DE); Bertram Cezanne, Mörfelden-Walldorf (DE); Johannes Gleitz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 524 days.

(21) Appl. No.: 10/551,670

(22) PCT Filed: Mar. 9, 2004

(86) PCT No.: PCT/EP2004/002405

§ 371 (c)(1),
(2), (4) Date: Sep. 30, 2005

(87) PCT Pub. No.: WO2004/087695

PCT Pub. Date: Oct. 14, 2004

(65) Prior Publication Data

US 2006/0211692 A1  Sep. 21, 2006

(30) Foreign Application Priority Data

Apr. 3, 2003 (DE) ................................ 103 15 377
Jun. 18, 2003 (DE) ................................ 103 27 428
Jun. 30, 2003 (DE) ................................ 103 29 295
Jul. 1, 2003 (DE) ................................ 103 29 457
Jul. 26, 2003 (DE) ................................ 103 34 174

(51) Int. Cl.
*C07D 413/02* (2006.01)
*A61K 31/5377* (2006.01)
(52) U.S. Cl. .................................... 544/141; 514/235.5
(58) Field of Classification Search .............. 514/235.2, 514/235.5, 423; 544/141; 548/537, 538
See application file for complete search history.

(56) References Cited

U.S. PATENT DOCUMENTS 4,217,130 A    8/1980  Tsuruta et al.
2003/0162787 A1*  8/2003  Bigge et al. ............ 514/252.03

FOREIGN PATENT DOCUMENTS

JP          63 232846         9/1988

OTHER PUBLICATIONS

Vippagunta et al., Crystalline solids, 2001, Advanced Drug Delivery Reviews, 48, pp. 3 and 18.*
Database Caplus 'Online! Chemical Abstracts Service, Columbus, Ohio, US: 1989, Ogura, Haruo et al: "A Process for Preparing Succinimidyl Carbamate or Oxamate-Containing Chromatography Carriers and Their Use for Enzyme Mobilization and Preparation of Chromatographic Chiral Stationary Phases" XP002283918 gefunden im STN Database accession No. 1989:595406.

* cited by examiner

*Primary Examiner*—Kamal A Saeed
*Assistant Examiner*—Kristin Bianchi
(74) *Attorney, Agent, or Firm*—Millen, White, Zelano & Branigan, P.C.

(57) ABSTRACT

Process for the preparation of compounds of the formula I in which R, $R^1$, $R^2$ and $R^3$ are as defined in Patent claim 1, and compounds of the formula IV in which R and $R^1$ are as defined in Patent claim 1, are intermediates for the preparation of the compounds of the formula I.

20 Claims, No Drawings

METHOD FOR THE PRODUCTION OF PYRROLIDINE-1,2-DICARBOXYLIC ACID-1-(PHENYL(-AMIDE))-2(PHENYL(-AMIDE)) DERIVATIVES AND 1-(PHENYLCARBAMOYL)-PYRROLIDINE-2-CARBOXYLIC ACID DERIVATIVES AS INTERMEDIATE PRODUCTS

The invention relates to a process for the preparation of compounds of the formula I

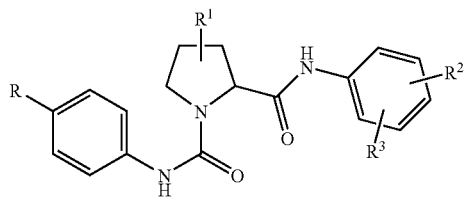

in which

R is Hal or C≡CH, $R^1$ is H, =O, Hal, A, OH, OA, A-COO—, A-CONH—, A-CONA-, $N_3$, $NH_2$, $NO_2$, CN, COOH, COOA, CONHA, $CONH_2$, $CON(A)_2$, O-allyl, O-propargyl, O-benzyl, =N—OH or =N-OA, $R^2$ is H, Hal or A, $R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-imino-pyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicycle[2.2.2]octan-3-on-2-yl, 5,6-dihydro-1 H-pyrimidin-2-oxo-1-yl, 2-oxo-1,3-oxazinan-3-yl or 4H-1,4-oxazin-4-yl, where the radicals may also be mono- or disubstituted by A or OA, A is unbranched, branched or cyclic alkyl having 1-10 carbon atoms, in which, in addition, 1-7H atoms may be replaced by F, Hal is F, Cl, Br or I, and pharmaceutically usable derivatives, solvates and stereoisomers thereof, including mixtures thereof in all ratios, characterised in that a) a compound of the formula II

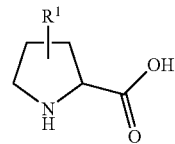

in which
$R^1$ is as defined above,
is reacted with a compound of the formula III

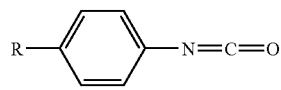

in which
R is as defined above, to give a compound of the formula IV

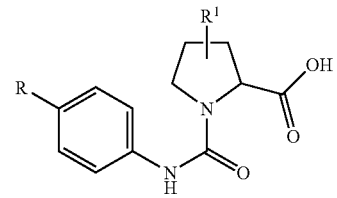

in which
R and $R^1$ are as defined above, b) a compound of the formula IV is then reacted with a compound of the formula V

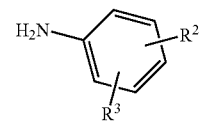

in which $R^2$ and $R^3$ are as defined above,
to give a compound of the formula I, and c) this is, if desired, converted into pharmaceutically usable derivatives and/or solvates thereof by converting a base or acid of the formula I into one of its salts.

The invention had the object of finding novel improved processes for the preparation of factor Xa inhibitors.

Compared with known processes from the prior art, the process according to the invention is shorter and more efficient.

Factor Xa inhibitors can be employed for combating and preventing thromboembolic diseases, such as thrombosis, myocardial infarction, arteriosclerosis, inflammation, apoplexia, angina pectoris, restenosis after angioplasty and claudicatio intermittens.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example by the method of G. F. Cousins et al. in *Circulation* 1996, 94, 1705-1712.

Inhibition of factor Xa can thus prevent the formation of thrombin.

The inhibition of factor Xa and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa and the measurement of the anticoagulant and antithrombotic activity can be determined by conventional in-vitro or in-vivo methods. A suitable method is described, for example, by J. Chang et al. in *Journal of Biological Chemistry* 1998, 273, 12089-12094.

A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59. The publications listed below describe an antitumoural action of TF-VII and factor Xa inhibitors for various types of tumour:

K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. Bromberg et al. in Thromb. Haemost. 1999; 82: 88-92.

WO 03/045912 describes a route which is longer by 2 steps, which proceeds via an N-protected pyrrolidine derivative, for example BOC-Pro:

*Helv. Chim. Acta* 1998, 81, 1254-1263 describes the reaction of primary amines with 4-chlorophenyl isocyanate (route A]).

As shown in route B], the reactive side-chain groups, such as OH, NH or SH, also react therein to give bisaddition products.

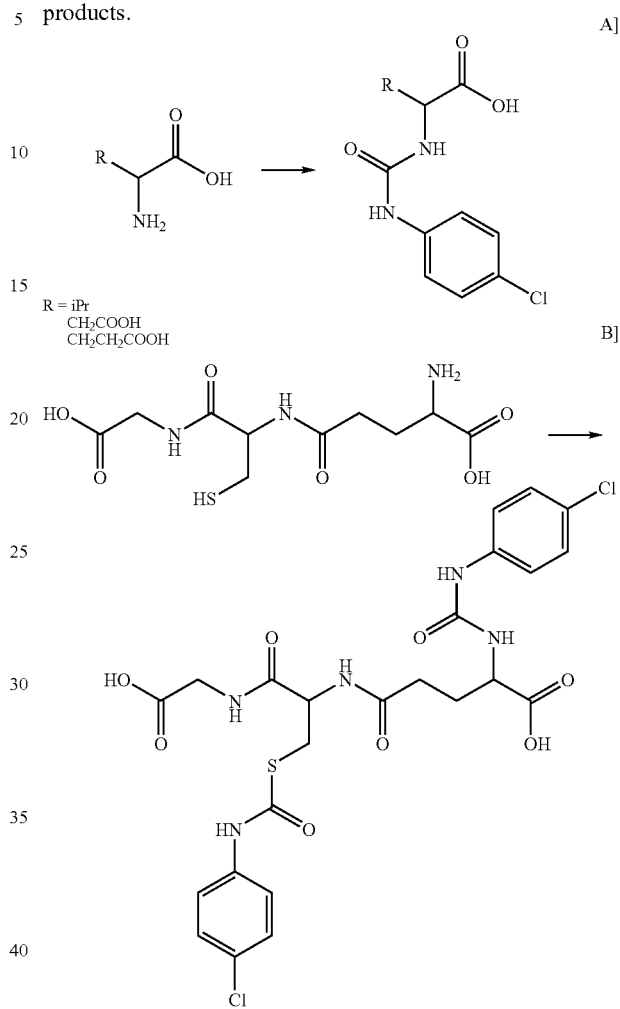

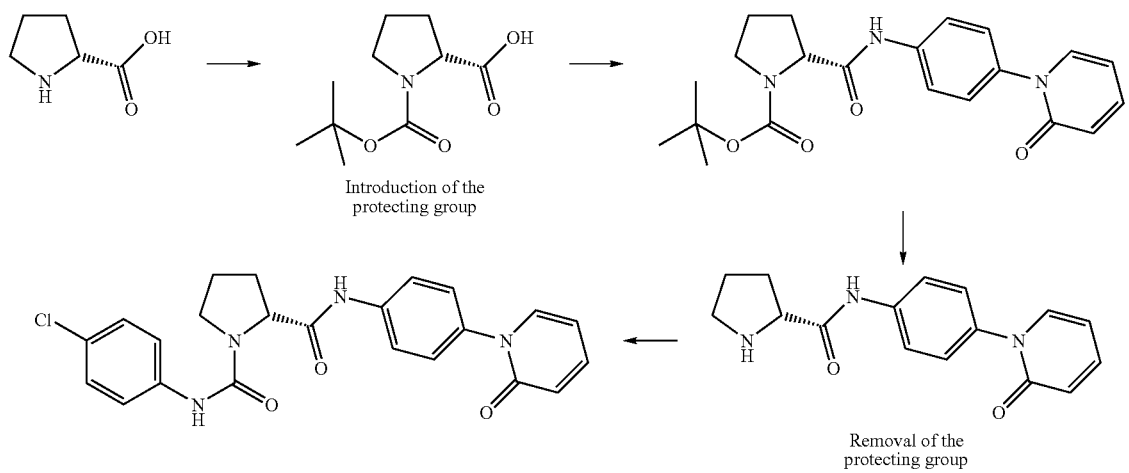

Introduction of the protecting group

Removal of the protecting group

The term pharmaceutically usable derivatives is taken to mean, for example, the salts of the compounds and so-called prodrug compounds.

Above and below, A denotes alkyl, is unbranched (linear) or branched, and has 1, 2, 3, 4, 5, 6, 7, 8, 9 or 10 carbon atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methyl-propyl, 1-ethyl-2-methylpropyl, 1,1,2- or 1,2,2-trimethylpropyl, furthermore preferably, for example, trifluoromethyl.

A is very particularly preferably alkyl having 1, 2, 3, 4, 5 or 6 carbon atoms, preferably methyl, ethyl, propyl, isopropyl, butyl, isobutyl, sec-butyl, tert-butyl, pentyl, hexyl or trifluoromethyl.

Hal is preferably F, Cl or Br, but also I.

The invention preferably relates to a process according to claim 1 for the preparation of compounds of the formula I in which R is F or Cl.

Preference is furthermore given to a process according to claim 1 or 2 for the preparation of compounds of the formula I in which
$R^1$ is H, =O, OH, OA, A-COO—, $N_3$, $NH_2$, O-allyl or O-propargyl.

Particular preference is given to a process according to claim 1 or 2 for the preparation of compounds of the formula I in which $R^1$ is H or OH.

Preference is furthermore given to a process according to claims 1-4 for the preparation of compounds of the formula I in which
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl.

Preference is furthermore given to a process according to claims 1-5 for the preparation of compounds of the formula I in which
A is unbranched or branched alkyl having 1-6 carbon atoms, in which, in addition, 1-3H atoms may be replaced by F.

Preference is furthermore given to a process according to one or more of claims 1-6 for the preparation of compounds of the formula I in which
R is Hal or C≡CH,
$R^1$ is H, OH or OA,
$R^2$ is H, Hal or A,
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl,
A is unbranched, branched or cyclic alkyl having 1-10 carbon atoms, in which, in addition, 1-7H atoms may be replaced by F,
Hal is F, Cl, Br or I,
and pharmaceutically usable derivatives, solvates and stereoisomers thereof, including mixtures thereof in all ratios.

Preference is furthermore given to a process according to one or more of claims 1-7 for the preparation of compounds of the formula I in which
R is F or Cl,
$R^1$ is H, =O, OH, OA, A-COO—, $N_3$, $NH_2$, O-allyl or O-propargyl,
$R^2$ is H, F or A,
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl,
A is unbranched or branched alkyl having 1-6 carbon atoms, in which, in addition, 1-3H atoms may be replaced by F,
and pharmaceutically usable derivatives, solvates and stereoisomers thereof, including mixtures thereof in all ratios.

Particular preference is given to a process according to one or more of claims 1-8 for the preparation of compounds of the formula 1 in which
R is F or Cl,
$R^1$ is H or OH,
$R^2$ is H, F or A,
$R^3$ is 3-oxomorpholin-4-yl,
A is unbranched or branched alkyl having 1-6 carbon atoms, in which, in addition, 1-3H atoms may be replaced by F,
and pharmaceutically usable derivatives, solvates and stereoisomers thereof, including mixtures thereof in all ratios.

Very particular preference is given to a process according to one or more of claims 1-15 for the preparation of compounds of the formula Ia

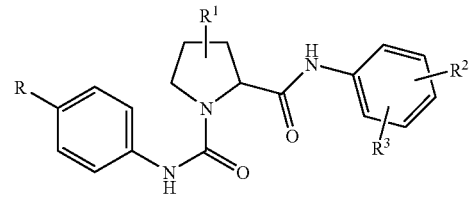

Ia in which
R is F or Cl,
$R^1$ is H or OH,
$R^2$ is H, F or A,
$R^3$ is 3-oxomorpholin-4-yl,
A is unbranched or branched alkyl having 1-6 carbon atoms, in which, in addition, 1-3H atoms may be replaced by F,
and pharmaceutically usable derivatives, solvates and stereoisomers thereof, including mixtures thereof in all ratios, characterised in that
a) a compound of the formula II

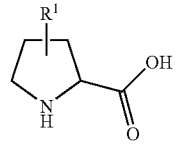

II in which
$R^1$ is H or OH, is reacted with a compound of the formula III

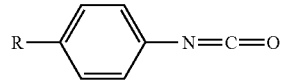

III in which
R is F or Cl, in aqueous alkali metal or alkaline earth metal carbonate or bicarbonate solution, at a temperature between 60° and 110° C., to give a compound of the formula IV

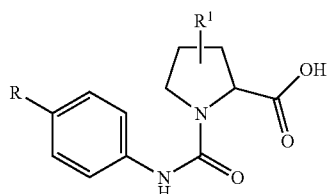

IV in which
R is F or C¹,
R¹ is H or OH,
b) a compound of the formula IV is then reacted with a compound of the formula V

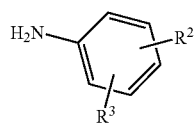

V in which
R² is H, F or A,
R³ is 3-oxomorpholin-4-yl,
A is unbranched or branched alkyl having 1-6 carbon atoms, in which, in addition, 1-3H atoms may be replaced by F,
in the presence of an auxiliary reagent with formation of a mixed anhydride, at a temperature between 10° and 70° C.,
to give a compound of the formula Ia, and
c) this is, if desired, converted into pharmaceutically usable derivatives and/or solvates thereof
by converting a base or acid of the formula Ia into one of its salts.

The compounds of the formula I or Ia can preferably be obtained by reacting compounds of the formula II with compounds of the formula III in a first step a).

The reaction is generally carried out in an inert solvent, in the presence of an acid-binding agent, preferably an alkali metal or alkaline earth metal hydroxide, carbonate or bicarbonate or another salt of a weak acid of the alkali or alkaline earth metals, preferably of potassium, sodium, calcium or caesium, such as, for example, NaOH, sodium carbonate, potassium carbonate, caesium carbonate or NaHCO₃.

Particular preference is given to NaHCO₃.

It may also be favourable to add an organic base, such as triethylamine, dimethylaniline, pyridine or quinoline. The reaction time is between a few minutes and 14 days, preferably between one and ten hours, depending on the conditions used, and the reaction temperature is between about 0° and 150°, normally between 20° and 130°, preferably between 60° and 110°, very particularly preferably between 70° and 90° C.

Examples of suitable inert solvents are water; hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone, isobutyl methyl ketone (IBMK) or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to water.

In a second step, compounds of the formula IV are reacted with compounds of the formula V.

The reaction is preferably carried out in the presence of an auxiliary reagent which forms an intermediate derivative with the OH group of the carboxylic acid, such as, for example, a mixed anhydride, an activated ester, an imidazolide or is converted into an alkylsulfonyloxy group having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

The coupling can be carried out using various condensation reagents, such as carbodiimides, carbodiimidazole, those of the uronium type, such as TBTU, and acid halide or activated ester methods. Activated esters are advantageously formed in situ, for example by addition of HOBt or N-hydroxysuccinimide.

Preference is given to the formation of a mixed anhydride.

Particular preference is given here to the use of ethyl 2-ethoxy-1,2-dihydroquinoline-1-carboxylate (EEDQ).

The reaction is generally carried out in an inert solvent.

The reaction time is between a few minutes and 14 days, preferably between one and twenty hours, depending on the conditions used, and the reaction temperature is between about 0° and 150°, normally between 0° and 90°, preferably between 10° and 70°, particularly preferably between 15° and 30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents, particularly preferably tetra hydrofuran.

A base of the formula I, Ia or of the formula IV can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethyl-acetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, or laurylsulfuric acid. Salts with physiologically unacceptable acids, for example picrates, can be used for the isolation and/or purification of the compounds of the formula I.

On the other hand, compounds of the formula I, Ia or IV can be converted into the corresponding metal salts, in particular alkali metal or alkaline earth metal salts, or into the corresponding ammonium salts using bases (for example sodium hydroxide, potassium hydroxide, sodium carbonate or potassium carbonate).

It is also possible to use physiologically acceptable organic bases, such as, for example, ethanolamine.

The invention furthermore relates to compounds of the formula IV

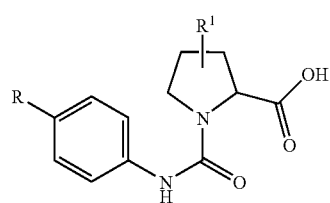

IV in which
R is Hal or C—CH,
R$^1$ is H, =O, Hal, A, OH, OA, A-COO—, A-CONH—, A-CONA-, N$_3$, NH$_2$, NO$_2$, CN, COOH, COOA, CONH$_2$, CONHA, CON(A)$_2$, O-allyl, O-propargyl, O-benzyl, =N—OH or =N-OA,
A is unbranched, branched or cyclic alkyl having 1-10 carbon atoms, in which, in addition, 1-7H atoms may be replaced by F,
Hal is F, Cl, Br or I,
and pharmaceutically usable derivatives, solvates and stereoisomers thereof, including mixtures thereof in all ratios.

The invention also relates to the optically active forms (stereoisomers), the enantiomers, the racemates, the diastereomers and the hydrates and solvates of the compounds according to the invention.

The term solvates of the compounds is taken to mean adducts of inert solvent molecules onto the compounds which form owing to their mutual attractive force. Solvates are, for example, mono- or dihydrates or alcoholates.

The term pharmaceutically usable derivatives is taken to mean, for example, the salts of the compounds according to the invention and so-called prodrug compounds.

The term prodrug derivatives is taken to mean compounds of the formula I which have been modified by, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61-67 (1995).

The invention also relates to mixtures of the compounds of the formula IV according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

In particular, the compounds of the formula IV can be used in processes for the preparation of compounds of the formula I.

Other ethynyl derivatives are described in WO 02/079145 as factor Xa inhibitors.

Other aromatic amides are described in WO 99/00121 and in WO 00/39118. Aromatic amidine derivatives having an antithrombotic action are disclosed, for example, in EP 0 540 051 B1. Cyclic guanidines for the treatment of thromboembolic diseases are described, for example, in WO 97/08165. Aromatic heterocyclic compounds having a factor Xa-inhibitory activity are disclosed, for example, in WO 96/10022. Substituted N-[(aminoiminomethyl)phenylalkyl]azaheterocyclylamides as factor Xa inhibitors are described in WO 96/40679.

For all radicals which occur more than once, their meanings are independent of one another.

A denotes alkyl, is unbranched (linear) or branched and has 1, 2, 3, 4, 5, 6, 7, 8, 9 or 10 carbon atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 carbon atoms, preferably methyl, ethyl, propyl, isopropyl, butyl, isobutyl, sec-butyl, tert-butyl, pentyl, hexyl or trifluoromethyl.

Hal preferably denotes F, Cl or Br, but also 1.

R preferably denotes F or Cl.

R$^1$ preferably denotes H, =O, OH, OA, A-COO—, N$_3$, NH$_2$, O-allyl or O-propargyl, particularly preferably H or OH.

Particular preference is given to compounds of the formula IV selected from the group consisting of
(2R,4R)-1-(4-chlorophenylcarbamoyl)-4-hydroxypyrrolidine-2-carboxylic acid,
(2R)-1-(4-chlorophenylcarbamoyl)pyrrolidine-2-carboxylic acid.

Compounds of the formula IV according to the invention may be chiral owing to their molecular structure and may accordingly occur in various enantiomeric forms. They may therefore be in racemic or optically active form.

Since the pharmaceutical efficacy of the racemates or stereoisomers of the end products resulting from the intermediate compounds may be different, it may be desirable to use the enantiomers of the compounds according to the invention. In these cases, the end product or even the intermediates can be separated into enantiomeric compounds by chemical or physical measures known to the person skilled in the art or already employed as such in the synthesis.

In the case of racemic amines, diastereomers are formed from the mixture by reaction with an optically active resolving agent. Suitable resolving agents are, for example, optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline) or the various optically active camphorsulfonic acids. Also advantageous is chromatographic resolution of the enantiomers with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent

EXAMPLE 1

1-[(4-chlorophenyl)]-2-{[4-(3-oxomorpholin-4-yl)-phenyl]}-(2R,4R)-4-hydroxypyrrolidine-1,2-dicarboxamide is prepared analogously to the following scheme:

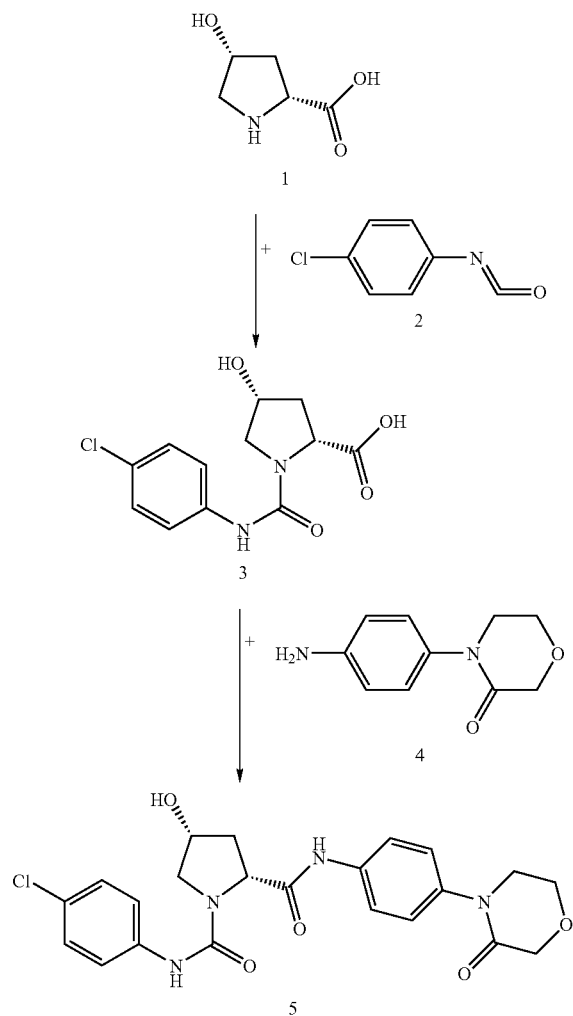

1.1 13.1 g (0.1 mol) of cis-hydroxy-D-proline are dissolved in 800 ml of NaHCO$_3$ solution (c=0.5 mol/l), 30.7 g (0.2 mol) of 4-chlorophenyl iso-cyanate are subsequently added, and the mixture is stirred at 80° C. for hours. The reaction mixture is cooled to RT, the precipitated symmetrical urea 1,3-bis(4-chlorophenyl)urethane is filtered off with suction and washed with water, and the aqueous phase is adjusted to pH=1 using about 40 ml of conc. HCl. The precipitated product is separated off, the aqueous phase is post-extracted with EA, and both organic parts are dried. The residue is then recrystallised from MTB ether, giving 23.3 g (81.8%) of (2R,4R)-1-(4-chlorophenylcarbamoyl)-4-hydroxypyrrolidine-2-carboxylic acid 3; m.p. 132-134°; MS (FAB): m/e=285 (M+H$^+$).

$^1$H NMR (DMSO-d$_6$) δ 12.00 (sbr, 1H), 8.39 (s, 1H), 7.54 (d, J=8.9 Hz, 2H), 7.26 (d, J=8.9 Hz, 2H), 4.41-4.24 (m, 2H), 3.66 (dd, J=5.7 and 5.8 Hz, 1H), 3.33 (dd, J=4.0 and 4.1 Hz, 1H), 2.40-2.25 (m, 1H), 1.96-1.81 (m, 1H).

Optical rotation: [α]$^{20}_D$=+43.7°; MeOH, c=0.0198 g/2 ml
C,H,N: Theoretical C, 50.63; H, 4.60; N, 9.84 Found C, 51.1; H, 4.6; N, 9.0.

1.2 14.24 g (0.05 mol) of 3, 9.61 g (0.05 mol) of aminophenylmorpholinone 4 and 12.37 g (0.05 mol) of ethyl 2-ethoxy-1,2-dihydroquinoline-1-carboxylate are dissolved in 400 ml of tetrahydrofuran at RT and stirred for 20 hours, during which a suspension forms. The precipitate is filtered off with suction, rinsed three times with THF and evaporated to dryness under reduced pressure, giving 15.9 g (69%) of 1-[(4-chlorophenyl)]-2-{[4-(3-oxo-morpholin-4-yl)-phenyl]}-(2R,4R)-4-hydroxypyrrolidine-1,2-dicarboxamide 5; m.p. 208-210°; MS (FAB): m/e=459 (M+H$^+$).

The following is obtained analogously to Example 1.1:
(2R)-1-(4-chlorophenylcarbamoyl)pyrrolidine-2-carboxylic acid, m.p. 173-175°,

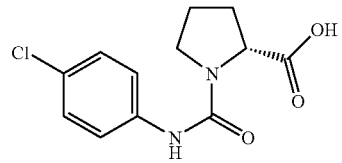

MS (FAB): m/e=269 (M+H$^+$);
$^1$H NMR (DMSO-d$_6$) δ 12.37 (sbr, 1H), 8.37 (s, 1H), 7.53 (d, J=8.9 Hz, 2H), 7.26 (d, J=8.9 Hz, 2H), 4.32 (dd, J=3.5 Hz, 1H), 3.60-3.41 (m, 2H), 2.27-2.07 (m, 1H), 2.00-1.81 (m, 3H).

Optical rotation: [α]$^{20}_D$=+60.9°; MeOH, c=0.0189 g/2 ml
C,H,N: Theoretical C, 53.64; H, 4.88; N, 10.43 Found C, 53.6; H, 5.1; N, 10.4.

EXAMPLE 2

The following compounds are obtained analogously to Example 1:

1-[(4-chlorophenyl)]-2-{[4-(3-oxomorpholin-4-yl)phenyl]}-(2R)-pyrrolidine-1,2-dicarboxamide, 1-[(4-chlorophenyl)]-2-{[3-methyl-4-(3-oxomorpholin-4-yl)phenyl]}-(2R)-pyrrolidine-1,2-dicarboxamide, 1-[(4-chlorophenyl)]-2-{[3-methyl-4-(3-oxomorpholin-4-yl)phenyl]}-(2R,4R)-4-hydroxypyrrolidine-1,2-dicarboxamide, 1-[(4-chlorophenyl)]-2-{[4-(3-oxomorpholin-4-yl)phenyl]}-(2S,4R)-4-hydroxypyrrolidine-1,2-dicarboxamide, 1-[(4-chlorophenyl)]-2-{[2-fluoro-4-(3-oxomorpholin-4-yl)phenyl]}-(2R)-pyrrolidine-1,2-dicarboxamide, 1-[(4-chlorophenyl)]-2-{[4-(3-oxomorpholin-4-yl)phenyl]}-(2R,4S)-4-hydroxypyrrolidine-1,2-dicarboxamide, 1-[(4-chlorophenyl)]-2-{[3-fluoro-4-(3-oxomorpholin-4-yl)phenyl]}-(2R)-pyrrolidine-1,2-dicarboxamide, 1-[(4-chlorophenyl)]-2-{[3-trifluoromethyl-4-(3-oxomorpholin-4-yl)-phenyl]}-(2R)-pyrrolidine-1,2-dicarboxamide, 1-[(4-chlorophenyl)]-2-{[2-fluoro-4-(3-oxomorpholin-4-yl) phenyl]}-(2R,4R)-4-hydroxypyrrolidine-1,2-dicarboxamide,
1-[(4-chlorophenyl)]-2-{[4-(3-oxomorpholin-4-yl)phenyl]}-(2R,4S)-4-azidopyrrolidine-1,2-dicarboxamide,
1-[(4-chlorophenyl)]-2-{[4-(3-oxomorphoiin-4-yl)phenyl]}-(2R,4S)-4-aminopyrrolidine-1,2-dicarboxamide,
1-[(4-chlorophenyl)]-2-{[4-(3-oxomorpholin-4-yl)phenyl]}-(2R,4R)-4-methoxypyrrolidine-1,2-dicarboxamide,
1-[(4-chlorophenyl)]-2-{[4-(3-oxomorpholin-4-yl)phenyl]}-(2R,4R)-4-acetoxypyrrolidine-1,2-dicarboxamide,
1-[(4-chlorophenyl)]-2-{[4-(3-oxomorpholin-4-yl)phenyl]}-(2R)-4-oxopyrrolidine-1,2-dicarboxamide,
1-[(4-chlorophenyl)]-2-{[3-methyl-4-(3-oxomorpholin-4-yl)phenyl]}-(2S)-pyrrolidine-1,2-dicarboxamide,
1-[(4-chlorophenyl)]-2-{[3-fluoro-4-(3-oxomorpholin-4-yl) phenyl]}-(2R,4R)-4-hydroxypyrrolidine-1,2-dicarboxamide,
1-[(4-chlorophenyl)]-2-{[4-(3-oxomorpholin-4-yl)phenyl]}-(2S,4S)-4-hydroxypyrrolidine-1,2-dicarboxamide,
1-[(4-chlorophenyl)]-2-{[4-(3-oxomorpholin-4-yl)phenyl]}-(2R,4R)-4-allyloxypyrrolidine-1,2-dicarboxamide,
1-[(4-chlorophenyl)]-2-{[4-(3-oxomorpholin-4-yl)phenyl]}-(2R,4R)-4-(prop-2-ynyloxy)pyrrolidine-1,2-dicarboxamide.

EXAMPLE 3

The reaction of L-hydroxyproline with 4-chlorophenyl isocyanate can be carried out analogously to Example 1.1, preferably also with one equivalent of chlorophenyl isocyanate, preferably in isobutyl methyl ketone (IBMK).

9.4 g (71.685 mmol) of L-hydroxyproline are dissolved in 71.68 ml of NaOH solution (c=1 mol/l) at from −2 to 0° C., a solution of 11.008 g (71.685 mmol) of 4-chlorophenyl isocyanate in 70 ml of IBMK is subsequently added, and the mixture is stirred at −1° C. for 1 hour. Conventional work-up gives 18.52 g of (2S,4R)-1-(4-chlorophenyl-carbamoyl)-4-hydroxypyrrolidine-2-carboxylic acid;
Yield: 91%.

The invention claimed is:
1. A process for preparing a compound of formula I

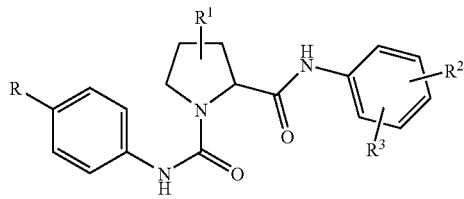

in which
R is Hal or C≡CH,
$R^1$ is H, =O, Hal, A, OH, OA, A—COO—, A—CONH—, A—CONA—, $N_3$, $NH_2$, $NO_2$, CN, COOH, COOA, $CONH_2$, CONHA, $CON(A)_2$, O-allyl, O-propargyl, O-benzyl, =N—OH or =N—OA,
$R^2$ is H, Hal or A,
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-imino-imidazolidin-1-yl, 2-imino1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl, which is optionally mono- or disubstituted by A or OA,
A is unbranched, branched or cyclic alkyl having 1-10 carbon atoms, in which 1-7 H atoms are optionally replaced by F,
Hal is F, Cl, Br or I,
or a pharmaceutically acceptable salt, mono- or dihydrate, alcoholate or stereoisomer thereof, comprising
a) reacting a compound of formula II

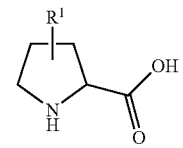

in which
$R^1$ is as defined above,
with a compound of formula III

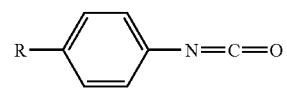

in which
R is as defined above,
to give a compound of formula IV

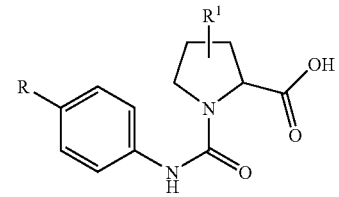

in which
R and $R^1$ are as defined above,
b) then reacting the compound of formula IV with a compound of formula V

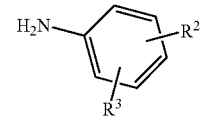

in which $R^2$ and $R^3$ are as defined above,
to give a compound of formula I, and
c) optionally converting the compound of formula I into a pharmaceutically acceptable salt, mono- or dihydrate or alcoholate thereof by converting a base or acid of the compound of formula I into one of its salts, or by bringing together the compound of formula I with water or an alcohol.

2. A process according to claim 1, wherein in the compound of formula I
R is F or Cl.

3. A process according to claim 1, wherein in the compound of formula I
$R^1$ is H, =O, OH, OA, A—COO—, $N_3$, $NH_2$, O-allyl or O-propargyl.

4. A process according to claim 1, wherein in the compound of formula I
$R^1$ is H or OH.

5. A process according to claim 1, wherein in the compound of formula I
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl.

6. A process according to claim 1, wherein in the compound of formula I
A is unbranched or branched alkyl having 1-6 carbon atoms, in which 1-3 H atoms are optionally replaced by F.

7. A process according to claim 1, wherein in the compound of formula I
R is Hal or C≡CH,
$R^1$ is H, OH or OA,
$R^2$ is H, Hal or A,
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl,
A is unbranched, branched or cyclic alkyl having 1-10 carbon atoms, in which 1-7 H atoms are optionally replaced by F, and
Hal is F, Cl, Br or I.

8. A process according to claim 1, wherein in the compound of formula I
R is F or Cl,
$R^1$ is H, =O, OH, OA, A—COO—, $N_3$, $NH_2$, O-allyl or O-propargyl,
$R^2$ is H, F or A,
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl, and
A is unbranched or branched alkyl having 1-6 carbon atoms, in which 1-3 H atoms are optionally replaced by F.

9. A process according to claim 1, wherein in the compound of formula I
R is F or Cl,
$R^1$ is H or OH,
$R^2$ is H, F or A,
$R^3$ is 3-oxomorpholin-4-yl, and
A is unbranched or branched alkyl having 1-6 carbon atoms, in which 1-3 H atoms are optionally replaced by F.

10. A process according to claim 1, in which the reaction in a) is carried out in an inert solvent or solvent mixture in the presence of an alkali or alkaline earth metal hydroxide, carbonate or bicarbonate.

11. A process according to claim 1, in which the reaction in a) is carried out in an aqueous $NaHCO_3$ solution.

12. A process according to claim 1, in which the reaction in a) is carried out at a temperature between 60° and 110° C.

13. A process according to claim 1, in which the reaction in b) is carried out in the presence of ethyl 2-ethoxy-1,2-dihydroquinoline-1-carboxylate (EEDQ).

14. A process according to claim 1, in which the reaction in b) is carried out at a temperature between 10° and 70° C.

15. A process according to claim 1, in which the reaction in b) is carried out in tetrahydrofuran.

16. A process for preparing a compound of formula Ia

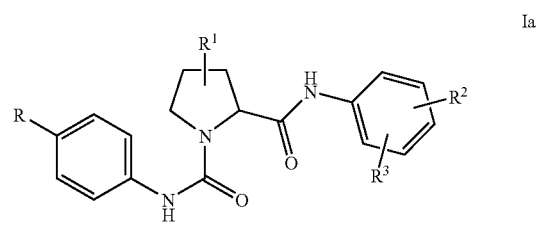

in which
R is F or Cl,
$R^1$ is H or OH,
$R^2$ is H, F or A,
$R^3$ is 3-oxomorpholin-4-yl,
A is unbranched or branched alkyl having 1-6 carbon atoms, in which 1-3 H atoms are optionally replaced by F,
or a pharmaceutically acceptable salt, mono- or dihydrate, alcoholate or stereoisomer thereof, comprising
a) reacting a compound of formula II

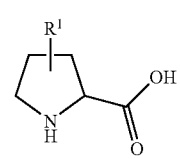

in which
$R^1$ is H or OH,
with a compound of formula III

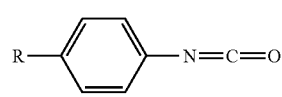

in which
R is F or Cl,
in an aqueous alkali metal or alkaline earth metal carbonate or bicarbonate solution at a temperature between 60° and 110° C., to give a compound of formula IV

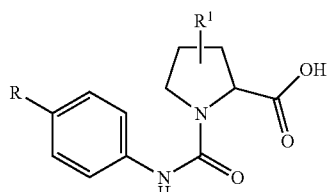

in which
R is F or Cl,
R¹ is H or OH,
b) then reacting the compound of formula IV with a compound of formula V

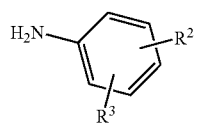

in which
R² is H, F or A,
R³ is 3-oxomorpholin-4-yl, and
A is unbranched or branched alkyl having 1-6 carbon atoms, in which 1-3 H atoms are optionally replaced by F,
in the presence of an auxiliary reagent with formation of a mixed anhydride at a temperature between 10° and 70° C.,
to give a compound of formula Ia, and
c) optionally converting the compound of formula Ia into a pharmaceutically acceptable salt, mono- or dihydrate or alcoholate thereof by converting a base or acid of the compound of formula Ia into one of its salts, or by bringing together the compound of formula Ia with water or an alcohol.

17. A process according to claim 1, wherein the compound of formula I is
- 1-[(4-chlor-phenyl)]-2-{[4-(3-oxo-morpholin-4-yl)-phenyl]}-(2R,4R)-4-hydroxypyrrolidine-1,2-dicarboxamide,
- 1-[(4-chlorophenyl)]-2-{[4-(3-oxomorpholin-4-yl)phenyl]}-(2R)-pyrrolidine-1,2-dicarboxamide,
- 1-[(4-chlorophenyl)]-2-{[3-methyl-4-(3-oxomorpholin-4-yl)phenyl]}-(2R)-pyrrolidine-1,2-dicarboxamide,
- 1-[(4-chlorophenyl)]-2-{[3-methyl-4-(3-oxomorpholin-4-yl)phenyl]}-(2R,4R)-4-hydroxypyrrolidine-1,2-dicarboxamide,
- 1-[(4-chlorophenyl)]-2-{[4-(3-oxomorpholin-4-yl)phenyl]}-(2S,4R)-4-hydroxypyrrolidine-1,2-dicarboxamide,
- 1-[(4-chlorophenyl)]-2-{[2-fluoro-4-(3-oxomorpholin-4-yl)phenyl]}-(2R)-pyrrolidine-1,2-dicarboxamide,
- 1-[(4-chlorophenyl)]-2-{[4-(3-oxomorpholin-4-yl)phenyl]}-(2R,4S)-4-hydroxypyrrolidine-1,2-dicarboxamide,
- 1-[(4-chlorophenyl)]-2-{[3-fluoro-4-(3-oxomorpholin-4-yl)phenyl]}-(2R)-pyrrolidine-1,2-dicarboxamide,
- 1-[(4-chlorophenyl)]-2-{[3-trifluoromethyl-4-(3-oxomorpholin-4-yl)-phenyl]}-(2R)-pyrrolidine-1,2-dicarboxamide,
- 1-[(4-chlorophenyl)]-2-{[2-fluoro-4-(3-oxomorpholin-4-yl)phenyl]}-(2R,4R)-4-hydroxypyrrolidine-1,2-dicarboxamide,
- 1-[(4-chlorophenyl)]-2-{[4-(3-oxomorpholin-4-yl)phenyl]}-(2R,4S)-4-azidopyrrolidine-1,2-dicarboxamide,
- 1-[(4-chlorophenyl)]-2-{[4-(3-oxomorpholin-4-yl)phenyl]}-(2R,4S)-4-aminopyrrolidine-1,2-dicarboxamide,
- 1-[(4-chlorophenyl)]-2-{[4-(3-oxomorpholin-4-yl)phenyl]}-(2R,4R)-4-methoxypyrrolidine-1,2-dicarboxamide,
- 1-[(4-chlorophenyl)]-2-{[4-(3-oxomorpholin-4-yl)phenyl]}-(2R,4R)-4-acetoxypyrrolidine-1,2-dicarboxamide,
- 1-[(4-chlorophenyl)]-2-{[4-(3-oxomorpholin-4-yl)phenyl]}-(2R)-4-oxopyrrolidine-1,2-dicarboxamide,
- 1-[(4-chlorophenyl)]-2-{[3-methyl-4-(3-oxomorpholin-4-yl)phenyl]}-(2S)-pyrrolidine-1,2-dicarboxamide,
- 1-[(4-chlorophenyl)]-2-{[3-fluoro-4-(3-oxomorpholin-4-yl)phenyl]}-(2R,4R)-4-hydroxypyrrolidine-1,2-dicarboxamide,
- 1-[(4-chlorophenyl)]-2-{[4-(3-oxomorpholin-4-yl)phenyl]}-(2S,4S)-4-hydroxypyrrolidine-1,2-dicarboxamide,
- 1-[(4-chlorophenyl)]-2-{[4-(3-oxomorpholin-4-yl)phenyl]}-(2R,4R)-4-allyloxypyrrolidine-1,2-dicarboxamide, or
- 1-[(4-chlorophenyl)]-2-{[4-(3-oxomorpholin-4-yl)phenyl]}-(2R,4R)-4-(prop-2-ynyloxy)pyrrolidine-1,2-dicarboxamide, or a pharmaceutically acceptable salt, mono- or dihydrate, alcoholate or stereoisomer thereof.

18. A process according to claim 1 for preparing a compound of formula I

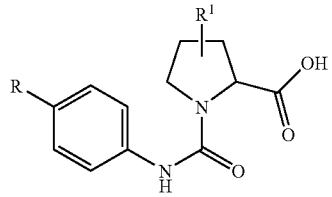

in which
R is Hal or C≡CH,
R¹ is H, =O, Hal, A, OH, OA, A—COO—, A—CONH—, A—CONA—, N₃, NH₂, NO₂, CN, COOH, COOA, CONH₂, CONHA, CON(A)₂, O-allyl, O-propargyl, O-benzyl, =N—OH or =N—OA,
R² is H, Hal or A,
R³ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-imino-imidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl, which is optionally mono- or disubstituted by A or OA,
A is unbranched, branched or cyclic alkyl having 1-10 carbon atoms, in which 1-7 H atoms are optionally replaced by F,
Hal is F, Cl, Br or I, or a pharmaceutically acceptable salt thereof, comprising
a) reacting a compound of formula II

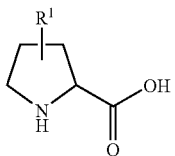
II in which
R¹ is as defined above,
with a compound of formula III

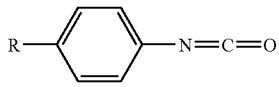
III in which
R is as defined above,
to give a compound of formula IV

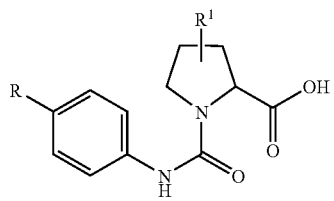
IV in which
R and R¹ are as defined above,
b) then reacting the compound of formula IV with a compound of formula V

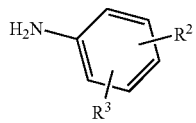
V in which R² and R³ are as defined above,
to give a compound of formula I, and
c) optionally concerting the compound of formula I into a pharmaceutically acceptable salt thereof by converting a base or acid of the compound of formula I into one of its salts.

19. A process according to claim 16 for preparing a compound of formula Ia

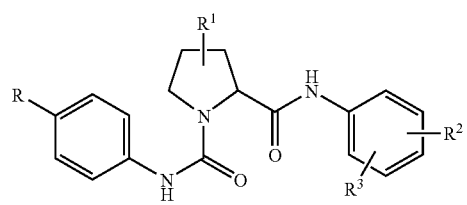
Ia in which
R is F or Cl,
R¹ is H or OH,
R² is H, F or A,
R³ is 3-oxomorpholin-4-yl,
A is unbranched or branched alkyl having 1-6 carbon atoms, in which 1-3 H atoms are optionally replaced by F, or a pharmaceutically acceptable salt thereof, comprising
a) reacting a compound of formula II

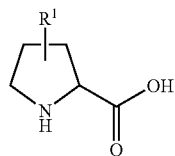
II in which
R is H or OH,
with a compound of formula III

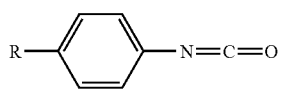
III in which
R is F or Cl,
in an aqueous alkali metal or alkaline earth metal carbonate or bicarbonate solution at a temperature between 60° and 110° C.,
to give a compound of formula IV

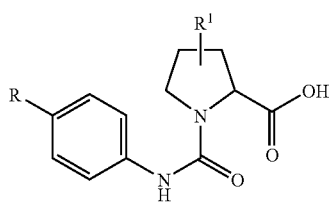
IV in which
R is F or Cl,
R¹ is H or OH,
b) then reacting the compound of formula IV with a compound of formula V

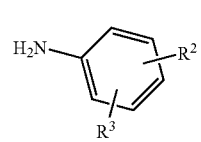
V in which
R² is H, F or A,
R² is 3-oxomorpholin-4-yl, and
A is unbranched or branched alkyl having 1-6 carbon atoms, in which 1-3 H atoms are optionally replaced by F,
in the presence of an auxiliary reagent with formation of a mixed anhydride at a temperature between 10° and 70° C.,
to give a compound of formula Ia, and
c) optionally converting the compound of formula Ia into a pharmaceutically acceptable salt thereof by converting a base or acid of the compound of formula Ia into one of its salts.

20. A process according to claim 18, wherein the compound of formula I is
1-[(4-chlor-phenyl)]-2-{[4-(3-oxo-morpholin-4-yl)-phenyl]}-(2R,4R)-4-hydroxypyrrolidine-1,2-dicarboxamide, 1-[(4-chlorophenyl)]-2-{[4-(3-oxomorpholin-4-yl)phenyl]}-(2R)-pyrrolidine-1,2-dicarboxamide, 1-[(4-chlorophenyl)]-2-{[3-methyl-4-(3-oxomorpholin-4-yl)phenyl]}-(2R)-pyrrolidine-1,2-dicarboxamide, 1-[(4-chlorophenyl)]-2-{[3-methyl-4-(3-oxomorpholin-4-yl)phenyl]}-(2R,4R)-4-hydroxypyrrolidine-1,2-dicarboxamide, 1-[(4-chlorophenyl)]-2-{[4-(3-oxomorpholin-4-yl)phenyl]}-(2S,4R)-4-hydroxypyrrolidine-1,2-dicarboxamide, 1-[(4-chlorophenyl)]-2-{[2-fluoro-4-(3-oxomorpholin-4-yl)phenyl]}-(2R)-pyrrolidine-1,2-dicarboxamide, 1-[(4-chlorophenyl)]-2-{[4-(3-oxomorpholin-4-yl)phenyl]}-(2R,4S)-4-hydroxypyrrolidine-1,2-dicarboxamide, 1-[(4-chlorophenyl)]-2-{[3-fluoro-4-(3-oxomorpholin-4-yl)phenyl]}-(2R)-pyrrolidine-1,2-dicarboxamide, 1-[(4-chlorophenyl)]-2-{[3-trifluoromethyl-4-(3-oxomorpholin-4-yl)-phenyl]}-(2R)-pyrrolidine-1,2-dicarboxamide, 1-[(4-chlorophenyl)]-2-{[2-fluoro-4-(3-oxomorpholin-4-yl)phenyl]}-(2R,4R)-4-hydroxypyrrolidine-1,2-dicarboxamide, 1-[(4-chlorophenyl)]-2-{[4-(3-oxomorpholin-4-yl)phenyl]}-(2R,4S)-4-azidopyrrolidine-1,2-dicarboxamide, 1-[(4-chlorophenyl)]-2-{[4-(3-oxomorpholin-4-yl)phenyl]}-(2R,4S)-4-aminopyrrolidine-1,2-dicarboxamide, 1-[(4-chlorophenyl)]-2-{[4-(3-oxomorpholin-4-yl)phenyl]}-(2R,4R)-4-methoxypyrrolidine-1,2-dicarboxamide, 1-[(4-chlorophenyl)]-2-{[4-(3-oxomorpholin-4-yl)phenyl]}-(2R,4R)-4-acetoxypyrrolidine-1,2-dicarboxamide, 1-[(4-chlorophenyl)]-2-{[4-(3-oxomorpholin-4-yl)phenyl]}-(2R)-4-oxopyrrolidine-1,2-dicarboxamide, 1-[(4-chlorophenyl)]-2-{[3-methyl-4-(3-oxomorpholin-4-yl)phenyl]}-(2S)-pyrrolidine-1,2-dicarboxamide, 1-[(4-chlorophenyl)]-2-{[3-fluoro-4-(3-oxomorpholin-4-yl)phenyl]}-(2R,4R)-4-hydroxypyrrolidine-1,2-dicarboxamide, 1-[(4-chlorophenyl)]-2-{[4-(3-oxomorpholin-4-yl)phenyl]}-(2S,4S)-4-hydroxypyrrolidine-1,2-dicarboxamide, 1-[(4-chlorophenyl)]-2-{[4-(3-oxomorpholin-4-yl)phenyl]}-(2R,4R)-4-allyloxypyrrolidine-1,2-dicarboxamide, or 1-[(4-chlorophenyl)]-2-{[4-(3-oxomorpholin-4-yl)phenyl]}-(2R,4R)-4-(prop-2-ynyloxy)pyrrolidine-1,2-dicarboxamide, or a pharmaceutically acceptable salt thereof.

\* \* \* \* \*

UNITED STATES PATENT AND TRADEMARK OFFICE
CERTIFICATE OF CORRECTION

PATENT NO. : 7,504,500 B2
APPLICATION NO. : 10/551670
DATED : March 17, 2009
INVENTOR(S) : Werner Mederski It is certified that error appears in the above-identified patent and that said Letters Patent is hereby corrected as shown below:

Column 13, line 67, reads "2-iminolH-pyrazin-l-yl," should read
-- 2-imino-1H-pyrazin-l-yl, --

Column 18, in claim 18, reads

" 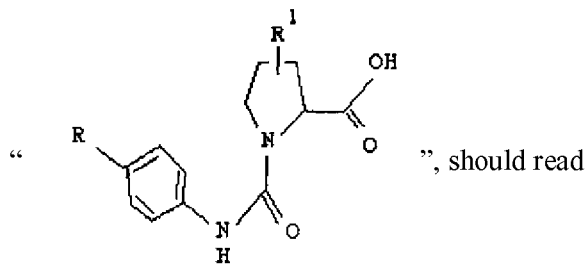 ", should read

-- 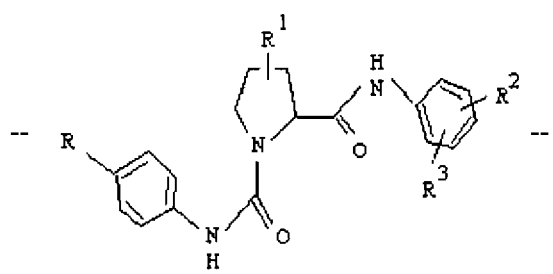 --

Column 20, line 12, reads "R is H or OH," should read -- $R^1$ is H or OH, --

UNITED STATES PATENT AND TRADEMARK OFFICE
CERTIFICATE OF CORRECTION

PATENT NO. : 7,504,500 B2
APPLICATION NO. : 10/551670
DATED : March 17, 2009
INVENTOR(S) : Werner Mederski It is certified that error appears in the above-identified patent and that said Letters Patent is hereby corrected as shown below:

Column 20, line 51, reads "$R^2$ is 3-oxomorpholin-4-yl," should read
-- $R^3$ is 3-oxomorpholin-4-yl, --

Signed and Sealed this

Sixteenth Day of June, 2009

JOHN DOLL
*Acting Director of the United States Patent and Trademark Office*